US009857287B2

(12) United States Patent
Dittrich et al.

(10) Patent No.: US 9,857,287 B2
(45) Date of Patent: Jan. 2, 2018

(54) PARTICULATE SENSOR DEVICE

(71) Applicants: Robert Bosch GmbH, Stuttgart (DE); Koninklijke Philips N.V., Eindhoven (NL)

(72) Inventors: Niklas Dittrich, Pliezhausen (DE); Frank Fischer, Gomaringen (DE); Reiner Schnitzer, Reutlingen (DE); Jochen Hellmig, Valkenswaard (NL); Gael Pilard, Wankheim (DE); Alexander Van der Lee, Venlo (NL)

(73) Assignees: ROBERT BOSCH GMBH, Stuttgart (DE); KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 15/130,517

(22) Filed: Apr. 15, 2016

(65) Prior Publication Data

US 2016/0313243 A1 Oct. 27, 2016

(30) Foreign Application Priority Data

Apr. 22, 2015 (DE) ........................ 10 2015 207 289

(51) Int. Cl.
*G01N 21/47* (2006.01)
*G01N 15/14* (2006.01)
(Continued)

(52) U.S. Cl.
CPC ..... *G01N 15/1431* (2013.01); *G01N 15/0205* (2013.01); *G01N 15/06* (2013.01);
(Continued)

(58) Field of Classification Search
CPC ........... G01N 15/1431; G01N 15/0205; G01N 15/06; G01N 15/1434; G01N 2015/1486;
(Continued)

(56) References Cited

U.S. PATENT DOCUMENTS 5,587,785 A * 12/1996 Kato ........................ G01P 3/366 356/28
5,943,130 A * 8/1999 Bonin ................ G01N 15/0205 356/237.5
6,459,093 B1 * 10/2002 Dieckmann ............... G01J 3/44 250/227.19
2006/0132770 A1 * 6/2006 Girvin ................ G01N 15/1459 356/338
2007/0063140 A1 * 3/2007 Liu .................... G01N 15/0205 250/301

(Continued)

*Primary Examiner* — Sang Nguyen
(74) *Attorney, Agent, or Firm* — Norton Rose Fulbright US LLP; Gerard Messina

(57) ABSTRACT

A particle sensor apparatus having an optical emitter device that is configured to emit an optical radiation so that a volume having at least one particle possibly present therein is at least partly illuminatable; an optical detector device having at least one detection surface that is struck by at least a portion of the optical radiation scattered at the at least one particle, at least one information signal regarding an intensity and/or an intensity distribution of the optical radiation striking the at least one detection surface being outputtable; and an evaluation device with which an information item regarding a presence of particles, a number of particles, a particle density, and/or at least one property of particles is identifiable and outputtable, the particle sensor apparatus also encompassing at least one lens element that is disposed so that the emitted optical radiation is focusable onto a focus region inside the volume.

13 Claims, 2 Drawing Sheets

(51) Int. Cl.

| | |
|---|---|
| ***G01N 15/02*** | (2006.01) |
| ***G01N 15/06*** | (2006.01) |
| *G01N 15/00* | (2006.01) |
| *G01N 15/10* | (2006.01) |

(52) U.S. Cl.

CPC . *G01N 15/1434* (2013.01); *G01N 2015/0046* (2013.01); *G01N 2015/0294* (2013.01); *G01N 2015/0693* (2013.01); *G01N 2015/1075* (2013.01); *G01N 2015/149* (2013.01); *G01N 2015/1486* (2013.01); *G01N 2015/1493* (2013.01); *G01N 2015/1497* (2013.01)

(58) Field of Classification Search

CPC ... G01N 2015/0046; G01N 2015/1075; G01N 2015/0693; G01N 2015/149; G01N 2015/1493; G01N 2015/1497; G01N 2015/0294

See application file for complete search history.

(56) References Cited

U.S. PATENT DOCUMENTS

2007/0263215 A1* 11/2007 Bachalo ............ G01B 9/02045 356/336
2008/0221812 A1* 9/2008 Pittaro .................. G01N 15/14 702/66
2008/0235966 A1* 10/2008 Klapper .................. G01C 9/06 33/366.23
2009/0316151 A1* 12/2009 Matula .............. G01N 15/1459 356/338
2011/0007299 A1* 1/2011 Moench ................. G01P 3/366 356/3
2013/0269424 A1* 10/2013 Jarrell ............... G01N 15/1429 73/61.48
2014/0268142 A1* 9/2014 Tropea .............. G01N 15/0211 356/340
2016/0238510 A1* 8/2016 Bachalo ............ G01N 15/1429

* cited by examiner

PARTICULATE SENSOR DEVICE

FIELD OF THE INVENTION

The present invention relates to a particle sensor apparatus.

BACKGROUND INFORMATION

FIG. 1 shows a scattered-light particle counter whose depicted components are contained, for example, in the scattered-light particle counter discussed in DE 10 2013 202 423 A1.

The scattered-light particle counter schematically depicted in FIG. 1 has a laser light source 10, a photodetector 12, and a measurement cell 14 through which an air stream 16 is drawn. A portion of measurement cell 14 is transilluminated by a laser beam 18 emitted from laser light source 10. If laser beam 18 strikes at least one particle 16*a* of air stream 16 inside the transilluminated portion of measurement cell 14, at least some photons of laser beam 18 are then scattered onto photodetector 12 as scattered output 20. (The non-scattered component of laser beam 18 strikes an absorber 22.) With the use of a conventional scattered-light particle counter of this kind it is said to be possible to ascertain, on the basis of scattered output 20 detected by way of photodetector 12, information regarding any particles 16*a* that may be present in air stream 16.

SUMMARY OF THE INVENTION

The present invention provides a particle sensor apparatus having the features described herein.

The particle sensor apparatus according to the present invention makes possible sufficiently high-intensity optical radiation in the focusing region because of the focusing of the emitted optical radiation onto the focus region itself, with use of an optical emitter device having weak emission. An intensity of the optical radiation scattered at the at least one particle in the focus region is thus also high. In particular, sufficiently high intensity of the optical radiation scattered from the particles in the focus region is ensured even for a small particle size even though the intensity of the scattered optical radiation is dependent on the particle size of the scattering particles. This also ensures that the optical detector device exhibits high sensitivity. The particle sensor apparatus according to the present invention thus enables accurate and (almost) error-free identification of the outputted information.

The particle sensor apparatus according to the present invention also exhibits, during operation thereof, a reduced power consumption as compared with conventional scattered-light particle counters. This facilitates the provision of energy to the particle sensor apparatus for operation thereof, for example by way of a battery.

As explained in more detail below, the particle sensor apparatus according to the present invention can also be manufactured inexpensively as compared with conventional scattered-light particle counters of reduced overall size. The particle sensor apparatus according to the present invention is thus also advantageously suitable for mobile use or as a sensor for a networked system.

In an advantageous embodiment of the particle sensor apparatus at least a portion of the optical radiation focused onto the focus region and at least partly scattered at the at least one particle in the focus region is focused by way of the at least one lens element onto the at least one detection surface. Further optical components on the particle sensor apparatus can be omitted thanks to this multifunctionality of the at least one lens element.

For example, the emitted optical radiation can be focusable by way of the at least one lens element onto a focus region having a focus length of less than 20 cm and/or a focus diameter of less than 1000 μm. In particular, the emitted optical radiation can be focusable by way of the at least one lens element onto a focus region having a focus length of between 1 and 3 cm and/or a focus diameter of between 1 and 20 μm.

In a further advantageous embodiment of the particle sensor apparatus the evaluation device is configured to identify an average particle size, a particle size distribution, an average particle mass, a particle mass distribution, an average particle shape, a particle shape distribution, an average particle speed, and/or a particle speed distribution as the at least one property of particles. The particle sensor apparatus is thus usable in versatile fashion.

The optical emitter device and the optical detector device may be embodied on and/or in one common chip. This facilitates miniaturization of the particle sensor apparatus.

In an inexpensive embodiment the optical emitter device encompasses a VCSE laser and/or VeCSE laser. In this case the optical detector device may encompass at least one photodiode integrated into a layer structure of the VCSE laser or VeCSE laser.

In a further embodiment of the particle sensor apparatus the emitted optical radiation and/or the scattered optical radiation are analyzed by way of the self-mixing interference effect. In other words, the self-mixing interference effect, which can be sensed e.g. by way of an integrated photodiode, is used to detect light scattered from the particle.

An optical detector device of this kind allows undesired ambient light signals to be automatically filtered out. Parasitic light incidence into the volume external to or internal to the apparatus thus degrades operation of the particle sensor apparatus less than in the case of a conventional scattered-light particle counter. Whereas with a conventional scattered-light particle counter reliable darkening of the measurement cell is a basic prerequisite for operation thereof, the particle sensor apparatus described here exhibits automatic "filtering out" of background signals.

In an advantageous refinement the particle sensor apparatus additionally encompasses a mirror device with which the focus region is shiftable one- or two-dimensionally inside the volume.

A sample volume to be investigated with regard to the particles can thus be scanned by the focus region.

In all the embodiments described here the particle sensor apparatus can be a particle detection apparatus and/or a particle counter apparatus.

Further features and advantages of the present invention will be explained below with reference to the Figures.

DETAILED DESCRIPTION

Figure 1:
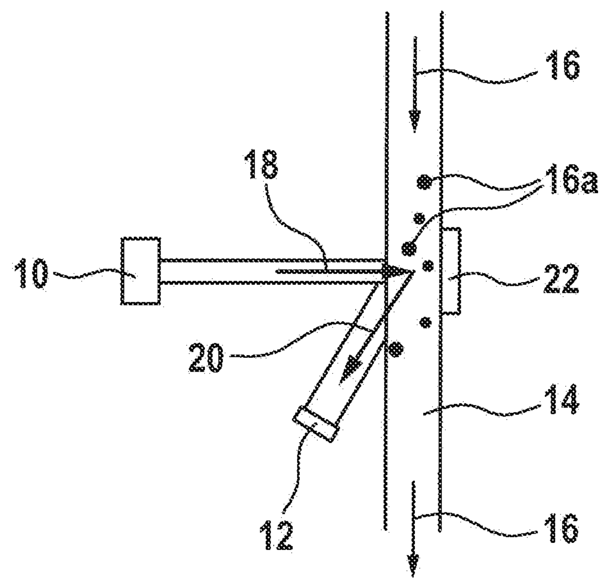
FIG. 1 shows a scattered-light particle counter.
Figure 2A:
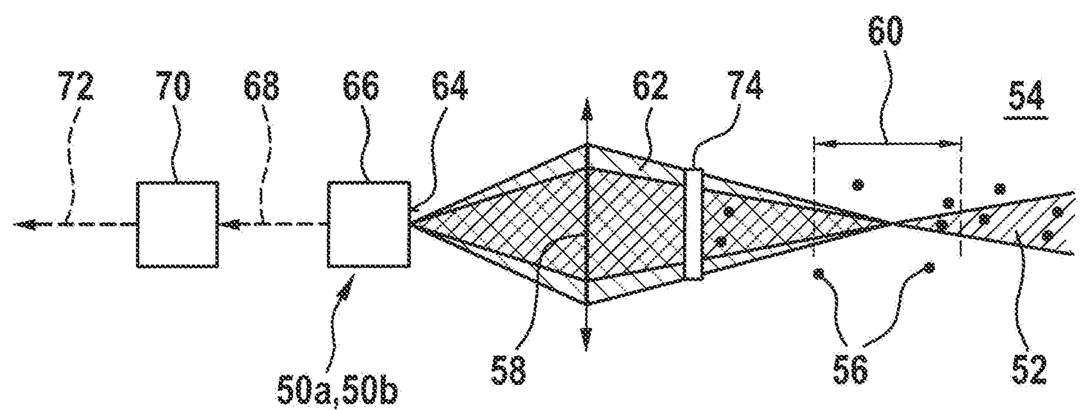
FIGS. 2*a* and 2*b* schematically depict a first embodiment of the particle sensor apparatus and a Fourier spectrum to explain its manner of operation.
Figure 2B:
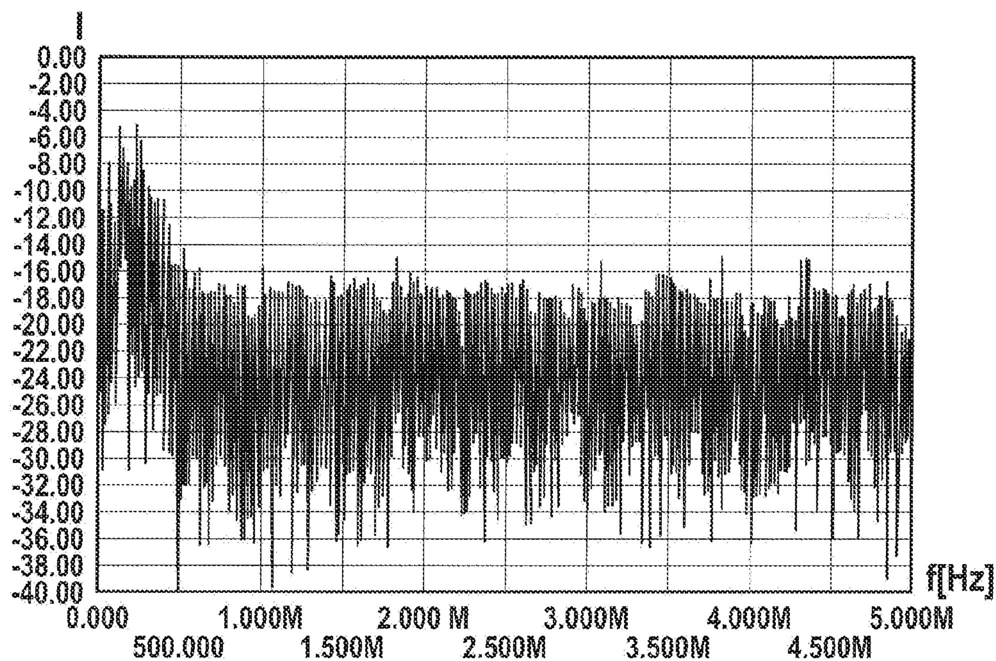

FIGS. 2*a* and 2*b* schematically depict a first embodiment of the particle sensor apparatus and a Fourier spectrum to explain its manner of operation.

The particle sensor apparatus schematically depicted in FIG. 2*a* has an optical emitter device 50*a* that is configured to emit an optical radiation 52 within an emission spectrum of optical emitter device 50*a*. The emission spectrum of optical emitter device 50*a* can be, for example, in a wavelength region from 350 nm to 1150 nm, in particular in the visible wavelength region. It is explicitly noted, however, that the emission spectrum of optical emitter device 50*a* is not limited to this wavelength region, in particular not to the visible wavelength region. At least a portion of the emission spectrum of optical emitter device 50*a* can thus also be located in the infrared region and/or in the UV region. In particular, optical emitter device 50*a* can also be configured to emit a monochromatic optical radiation 52. Optical emitter device 50*a* can also be configured to emit a polychromatic optical radiation 52.

Optical emitter device 50*a* can encompass in particular a laser 50*a*. If a pulsed optical radiation 52 is used for the particle sensor apparatus, optical emitter device 50*a* can also be a pulsed laser 50*a*. A laser 50*a* used for optical emitter device 50*a* can furthermore emit as optical radiation 52 a laser beam having (almost) any beam diameter. The usability of a laser 50*a* for optical emitter device 50*a* thus does not represent (almost) any basic prerequisite for the laser beam emitted as optical radiation 52.

In an advantageous embodiment optical emitter device 50*a* is/encompasses a vertical cavity surface emitting (VCSE) laser 50*a*. A VCSE laser 50*a* of this kind, which is often also referred to as a "surface emitter" 50*a*, is as a rule a semiconductor laser in which optical radiation 52 is emitted perpendicularly to a functionalized semiconductor chip plane. The use of VCSE laser 50*a* for optical emitter device 50*a* improves miniaturizability of the particle sensor apparatus.

The particle sensor apparatus schematically depicted in FIG. 2*a* can be used to detect or investigate particles 56 that are possibly present in at least a portion of a volume 54. The respective volume 54 can be a volume 54 internal to the apparatus, for example a sample chamber/measurement chamber of the particle sensor apparatus. The particle sensor apparatus can also, however, be configured to detect or investigate particles 56 in at least a portion of volume 54 external to the apparatus. In this case the particle sensor apparatus may be capable of being disposed on volume 54 external to the apparatus in such a way that those functions of its components which are described below can be performed.

Volume 54 (having the at least one particle 56 possibly present therein) can in all cases be illuminatable at least partly with optical radiation 52 emitted from optical emitter device 50*a*. The particle sensor apparatus furthermore has at least one lens element/focusing element 58 that is disposed so that optical radiation 52 that is emitted (from optical emitter device 50*a*) is focusable/focused by way of the at least one lens element/focusing element 58 onto a focus region 60 inside volume 54. Optical radiation 52 that is emitted (from optical emitter device 50*a*) may be focusable onto focus region 60 inside volume 54 by way of the at least one lens element/focusing element 58 in such a way that a high intensity of the emitted optical radiation 52 exists only inside focus region 60, while at the same time a remaining region of volume 54 outside focus region 60 exhibits an appreciably lower intensity of the emitted optical radiation 52.

A particular focus point/focus region 60 has a diameter of less than 1000 μm. In particular, a diameter from 1 to 20 μm is advantageous. It is thereby possible to ensure, even in the context of a low intensity of optical radiation 52 that is emitted (from optical emitter device 50*a*), that an increased intensity of the emitted optical radiation 52 exists inside focus region 60. Even in the context of a comparatively weak emission from optical emitter device 50, the intensity of optical radiation 52 that is emitted (from optical emitter device 50*a*) is thus sufficiently high to ensure an optically easily detectable scattered output 62 at the at least one particle 56 present in focus region 60. The easy detectability of the scattered output produced by the at least one particle 56 present in focus region 60 furthermore improves an accuracy of results in the context of investigation of a possible presence of particles 56 and/or in the context of ascertaining their properties.

This makes possible detection and/or investigation of particles 56 (almost) independently of a material present in volume 54, for example a gas and/or a liquid. Usability of the particle sensor apparatus is thus also almost not limited to the material (in which particles 56 may be present). This increases the usability of the particle sensor apparatus.

The at least one lens element/focusing element 58" can be understood as any optical element suitable for focusing light. The at least one lens element/focusing element 58 can be, for example, a (single) focusing lens 58. An inexpensive component can thus be used on the particle sensor apparatus as the at least one lens element/focusing element 58.

A particular focus length is less than 20 cm; 1 to 3 cm is believed to be particularly advantageous.

The particle sensor apparatus also has an optical detector device 50*b* having at least one detection surface 64. The at least one detection surface 64 is disposed so that at least a portion of the optical radiation (constituting scattered output 62) that is emitted from optical emitter device 50*a* and is at least partly scattered at the at least one particle 56 (in focus region 60) strikes the at least one detection surface 64. The focusing of optical radiation 52 (emitted from optical emitter device 50*a*) onto focus region 60, and the high intensity, produced thereby, of optical radiation 52 in focus region 60, ensure that even with a small number of particles 56 in focus region 60 and/or with a small particle size in focus region 60, a scattered output 62 still strikes the at least one detection surface 64 with an easily and reliably detectable intensity. In other words, because of the intense focusing, a narrowly specifiable distance region is defined as focus region 60, in which region a sufficiently high intensity of scattered output 62 can reliably be generated so that a significant scattered signal is ensured even in a context of a small number of particles 64 and/or a small particle size in focus region 60. A high and reliable sensitivity of the particle sensor apparatus, even to few particles 56 having a small particle size, is thus created.

The comparatively high intensity of scattered output 62 (even with a small number of particles 64 and/or a small particle size in focus region 60) also permits an inexpensive and space-saving embodiment of optical detector device 50*b*. Inexpensive detectors/photodiodes that require little installation space can thus be used on the particle sensor apparatus for optical detector device 50*b*.

Optical emitter device 50*a* and optical detector device 50*b* do not need to be understood as separately embodied devices. Optical emitter device 50*a* and optical detector 50*b* can instead be embodied as an optical emitter and detector device 50*a* and 50*b*. For example, optical emitter device 50*a* and optical detector device 50*b* can also be embodied on and/or in one common chip 66.

If optical emitter device 50*a* encompasses at least one VCSE laser and/or VeCSE laser 50*a*, then at least one photodiode, integrated into a layer structure of VCSE laser or VeCSE laser 50*a*, may be incorporated into optical detector device 50*b*. An optical emitter and detector device 50*a* and 50*b* of this kind, or the corresponding chip 66, can be referred to as an integrated self-mixing VCSEL (SMI-VCSEL) sensor 66. With a VCSEL sensor 66 of this kind, detection of scattered output 62 striking the at least one detection surface 64 is accomplished by interference of the emission with the incoming scattered output 62. In VCSEL sensor 66 a light incidence onto the at least one detection surface 64 which is not attributable to scattered output 62 (from the at least one particle 56 present in a focus region 60) is therefore automatically filtered out. This therefore eliminates the conventional need to shield volume 54 from ambient light in order to detect or investigate particles 56. The cost and the installation space requirement for light shielding apparatuses on the particle sensor apparatus are thus eliminated.

With common integration of devices 50*a* and 50*b* into chip 66, furthermore at least a portion of optical radiation/scattered output 62 focused onto focus region 60 and at least partly scattered at the at least one particle 56 in focus region 60 can be concentrated by way of the at least one lens element/focusing element 58 back onto the at least one detection surface 64. Thanks to this multifunctionality of the at least one lens element/focusing element 58, for example the (single) focusing lens 58, further optical components on the particle sensor apparatus can be omitted. It is furthermore possible to ensure in this fashion that what strikes the at least one detection surface 64 is (almost) exclusively scattered output 62 from focus region 60. The at least one lens element/focusing element 58, such as in particular the (single) focusing lens 58, thus also creates a further "spatially resolved filtering" of undesired scattered radiation out of the remaining region of volume 54 (outside focus region 60). This improves the detection accuracy of the particle sensor apparatus and reduces its error rate.

The range of embodiment of the particle sensor apparatus is not limited, however, to common integration of devices 50*a* and 50*b* on chip 66, or to a specific chip type of common chip 66.

Optical detector device 50*b* is configured to output at least one information signal/sensor signal 68 regarding an intensity and/or an intensity distribution of optical radiation/scattered output 62 striking the at least one detection surface 64. The particle sensor apparatus furthermore also has an evaluation device 70 with which, in consideration of the at least one information signal/sensor signal 68, an information item 72 regarding a presence of particles 56, a number of particles, a particle density, and/or a property of particles 56 can be identified and outputted. For example, evaluation device 70 can be configured to identify an average particle size, a particle size distribution, an average particle mass, a particle mass distribution, an average particle shape, a particle shape distribution, an average particle speed, and/or a particle speed distribution as the at least one property of particles 56.

FIG. 2*b* shows a coordinate system whose abscissa reproduces a frequency f (in hertz) and whose ordinate reproduces an intensity I for an SMI VCSEL sensor. A Fourier spectrum/Fourier transformation of an intensity distribution is plotted as an example of a possible information signal/sensor signal 68 of optical detector device 50*b*. A presence of particles 56, and their speeds, can be detected/measured on the basis of frequency bands that occur. (An average particle size of particles 56 used for this experiment was 3 μm.) It is evident that individual particles are also detectable by way of the particle sensor apparatus. FIG. 2*b* is to be interpreted, however, only as an example.

As an advantageous refinement, the particle sensor apparatus schematically depicted in FIG. 2*a* additionally has a mirror device 74 (depicted merely schematically) with which focus region 60 is shiftable one- or two-dimensionally inside volume 64. Mirror device 74 can have, for example, a single mirror that is adjustable around a pivot axis or around two pivot axes. Mirror device 74 can also encompass two mirrors adjustable around a pivot axis, the two pivot axes of the various mirrors being oriented in tilted, which may be perpendicular, fashion with respect to one another. The at least one mirror of mirror device 74 can be, for example, a MEMS mirror. An adjustment range of the at least one mirror of mirror device 74 may be less than 45°, in particular less than 20°. The adjustment range of the at least one mirror of mirror device 74 can, however, be up to 360°.

Equipping the particle sensor apparatus with mirror device 74 makes it possible to scan a comparatively large region of volume 54, in particular the entirety of volume 54, even though focus region 60 being investigated currently (within a short time interval) remains small. It is therefore no longer necessary to convey particles 56 actively (e.g. by way of a flow of air or liquid) into focus region 60. Suction and/or pump apparatuses on the particle sensor apparatus can thus be omitted.

Figure 3:
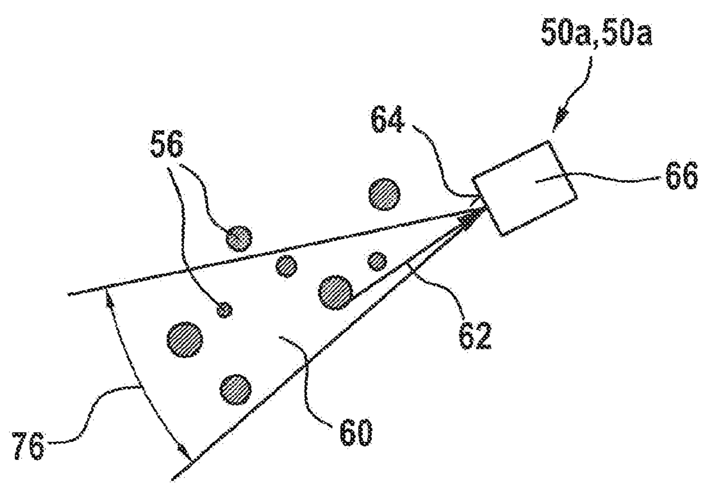
FIG. 3 schematically depicts a second embodiment of the particle sensor apparatus.

FIG. 3 schematically depicts a second embodiment of the particle sensor apparatus.

The particle sensor apparatus schematically depicted in FIG. 3 likewise has an optical system that causes the emitted optical radiation 52 to be focused onto a focus region 60 (in the midst of a beam path). What is achieved thereby is that an elevated luminance occurs in focus region 60, and an intensity of scattered output 62 out of focus region 60 is increased.

In this case as well, scattered output 62 is generated by the at least one particle 56 in focus region 60 and is directed via the optical system back to a common chip 66 of devices 50*a* and 50*b*. Only particles 56 that are located in (or near) focus region 60 generate a scattered output incident onto the at least one detection surface 64, while the undesired scattered radiation from a remaining region of volume 54 (outside focus region 60) can be (spatially and spectrally) filtered out.

It is evident that focus region 60 can be shifted by way of mirror device 74 in at least one spatial direction 76 in such a way that a two-dimensional fan-shaped or three-dimensional funnel-shaped region of volume 54 can be scanned. By way of such scanning of focus region 60, an enlarged region can thus be investigated with regard to the presence of particles 56 or with regard to their properties. A result thereof is, for example, that the measurement time for e.g. a statistically relevant average particle density per volume can be greatly reduced.

All the above-described embodiments of the particle sensor apparatus are usable as a particle detection apparatus and/or particle counter apparatus. They enable focusing of the emitted radiation 52 in such a way that only scattered output 62 from particles 56 that are located in focus region 60 at approximately +/−20% of the focal length strikes the at least one detection surface 64.

In all the embodiments described above the emitted optical radiation 52 is focusable by way of the at least one lens element/focusing element 58 onto a focus region 60 having a focus length of less than 20 cm and/or a focus diameter of less than 1000 μm. In particular, the focus length can be less than 5 cm. The focus length may be between 1 and 3 cm. The focus diameter can be less than 100 μm, which may be between 1 and 20 μm.

All the particle sensor apparatuses described above can have a compact design. In particular, the particle sensor apparatuses can respectively have an installation space requirement of less than 1 $cm^3$. Each of the particle sensor apparatuses described above is furthermore inexpensively manufacturable.

What is claimed is:

1. A particle sensor apparatus, comprising:

an optical emitter device configured to emit an optical radiation within an emission spectrum of the optical emitter device so that a volume external to the apparatus or internal to the apparatus having at least one particle possibly present therein is illuminatable at least partly with the emitted optical radiation;

an optical detector device having at least one detection surface, wherein the at least one detection surface is disposed so that at least a portion of the optical radiation emitted from the optical emitter device and at least partly scattered at the at least one particle strikes the at least one detection surface, and wherein the optical detector device is configured to output at least one information signal regarding at least one of an intensity and an intensity distribution of the optical radiation striking the at least one detection surface;

an evaluation device with which, in consideration of the at least one information signal, an information item regarding a presence of particles, a number of particles, a particle density, and/or at least one property of particles is identifiable and outputtable; and at least one lens element disposed so that the emitted optical radiation is focusable by the at least one lens element onto a focus region inside the volume;

wherein the optical emitter device encompasses at least one VCSE laser and/or VeCSE laser; and wherein the optical detector device encompasses at least one photodiode integrated into a layer structure of the VCSE laser and/or VeCSE laser of the optical emitter device.

2. The particle sensor apparatus of claim 1, wherein at least a portion of the optical radiation focused onto the focus region and at least partly scattered at the at least one particle in the focus region is focusable by the at least one lens element onto the at least one detection surface.

3. The particle sensor apparatus of claim 1, wherein the emitted optical radiation is focusable by the at least one lens element onto the focus region inside the volume, the at least one lens element having a focus length of less than 20 cm and/or a focus diameter of less than 1000 μm.

4. The particle sensor apparatus of claim 1, wherein the evaluation device is configured to identify at least one of an average particle size, a particle size distribution, an average particle mass, a particle mass distribution, an average particle shape, a particle shape distribution, an average particle speed, and a particle speed distribution as the at least one property of the particles.

5. The particle sensor apparatus of claim 1, wherein at least one of the emitted optical radiation and the scattered optical radiation is analyzed by the self-mixing interference effect.

6. The particle sensor apparatus of claim 1, wherein the particle sensor apparatus additionally encompasses a mirror device with which the focus region is shiftable one-dimensionally or two-dimensionally inside the volume.

7. The particle sensor apparatus of claim 1, wherein the particle sensor apparatus includes at least one of a particle detection apparatus and a particle counter apparatus.

8. The particle sensor apparatus of claim 1, wherein the optical emitter device and the optical detector device is embodied on and/or in one common chip.

9. A particle sensor apparatus, comprising:

an optical emitter device configured to emit an optical radiation within an emission spectrum of the optical emitter device so that a volume external to the apparatus or internal to the apparatus having at least one particle possibly present therein is illuminatable at least partly with the emitted optical radiation;

an optical detector device having at least one detection surface, wherein the at least one detection surface is disposed so that at least a portion of the optical radiation emitted from the optical emitter device and at least partly scattered at the at least one particle strikes the at least one detection surface, and wherein the optical detector device is configured to output at least one information signal regarding at least one of an intensity and an intensity distribution of the optical radiation striking the at least one detection surface;

an evaluation device with which, in consideration of the at least one information signal, an information item regarding a presence of particles, a number of particles, a particle density, and/or at least one property of particles is identifiable and outputtable; and at least one lens element disposed so that the emitted optical radiation is focusable by the at least one lens element onto a focus region inside the volume;

wherein the emitted optical radiation is focusable by the at least one lens element onto the focus region inside the volume, the at least one lens element having a focus length of between 1 and 3 cm and/or a focus diameter of between 1 and 20 μm.

10. The particle sensor apparatus of claim 9, wherein the optical emitter device encompasses at least one VCSE laser and/or VeCSE laser.

11. The particle sensor apparatus of claim 10, wherein the optical detector device encompasses at least one photodiode integrated into a layer structure of the VCSE laser and/or VeCSE laser or the optical emitter device.

12. The particle sensor apparatus of claim 9, wherein the optical emitter device and the optical detector device is embodied on and/or in one common chip.

13. A particle sensor apparatus, comprising:

an optical emitter device configured to emit an optical radiation within an emission spectrum of the optical emitter device so that a volume external to the apparatus or internal to the apparatus having at least one particle possibly present therein is illuminatable at least partly with the emitted optical radiation;

an optical detector device having at least one detection surface, wherein the at least one detection surface is disposed so that at least a portion of the optical radiation emitted from the optical emitter device and at least partly scattered at the at least one particle strikes the at least one detection surface, and wherein the optical detector device is configured to output at least one information signal regarding at least one of an intensity and an intensity distribution of the optical radiation striking the at least one detection surface;

an evaluation device with which, in consideration of the at least one information signal, an information item regarding a presence of particles, a number of particles, a particle density, and/or at least one property of particles is identifiable and outputtable; and at least one lens element disposed so that the emitted optical radiation is focusable by the at least one lens element onto a focus region inside the volume;

wherein the optical emitter device and the optical detector device is embodied on and/or in one common chip.

* * * * *